(12) United States Patent
Mimura et al.

(10) Patent No.: US 7,399,081 B2
(45) Date of Patent: Jul. 15, 2008

(54) OPHTHALMIC APPARATUS

(75) Inventors: Yoshiaki Mimura, Gamagori (JP);
Mikio Kurachi, Hazu-gun (JP); Naoto Honda, Okazaki (JP)

(73) Assignee: Nidek Co., Ltd. (JP)

( * ) Notice: Subject to any disclaimer, the term of this patent is extended or adjusted under 35 U.S.C. 154(b) by 617 days.

(21) Appl. No.: 10/811,824

(22) Filed: Mar. 30, 2004

(65) Prior Publication Data
US 2004/0189936 A1    Sep. 30, 2004

(30) Foreign Application Priority Data
Mar. 31, 2003 (JP) ............... 2003-095822
Feb. 27, 2004 (JP) ............... 2004-055424

(51) Int. Cl.
*A61B 3/10* (2006.01)
*A61B 3/00* (2006.01)
(52) U.S. Cl. .................. 351/205; 351/200
(58) Field of Classification Search ........... 351/200, 351/205, 208–209, 211–212, 221, 246–247
See application file for complete search history.

(56) References Cited

U.S. PATENT DOCUMENTS

| | | | |
|---|---|---|---|
| 5,299,573 A * | 4/1994 | Kobayashi | 600/401 |
| 5,463,430 A | 10/1995 | Isogai et al. | |
| 5,523,808 A * | 6/1996 | Kohayakawa | 351/210 |
| 5,680,196 A * | 10/1997 | Masuda | 351/208 |
| 5,689,325 A | 11/1997 | Isogai et al. | |
| 5,822,034 A * | 10/1998 | Shimashita et al. | 351/212 |
| 5,841,502 A * | 11/1998 | Miwa | 351/209 |
| 5,907,388 A | 5/1999 | Fujieda | |
| 5,909,269 A * | 6/1999 | Isogai et al. | 351/208 |
| 6,022,108 A * | 2/2000 | Yoshida et al. | 351/208 |
| 6,120,444 A * | 9/2000 | Miyakawa et al. | 600/401 |

FOREIGN PATENT DOCUMENTS

| | | |
|---|---|---|
| EP | 0 310 045 A1 | 4/1989 |
| EP | 0 850 591 A1 | 7/1998 |

(Continued)

OTHER PUBLICATIONS

EPO Search Report dated Jul. 16, 2004.

*Primary Examiner*—Scott J. Sugarman
*Assistant Examiner*—Dawayne A Pinkney
(74) *Attorney, Agent, or Firm*—Rader Fishman & Grauer PLLC; Ronald P. Kananen

(57) ABSTRACT

A multifunction ophthalmic apparatus, capable of efficiently measuring and examining eye characteristics respectively, has an measurement part including a unit blowing fluid to a cornea via a nozzle for measuring intraocular pressure of an examinee's eye, a reflection member having a reflection surface, arranged insertably and removably between the eye and the nozzle, an examination part storing an optical system, which photo-receives reflection light from the eye reflected by the member for examination, a main body storing the parts, a first unit moving the body relative to the eye in working distance direction, a second unit moving the measurement part relative to the body in the direction, a third moving unit inserting and removing the member, a device for emitting a switching signal between a first mode for examination and a second mode for measurement, and a unit controlling driving of the second and third moving units on the signal.

7 Claims, 6 Drawing Sheets

FOREIGN PATENT DOCUMENTS

| | | |
|---|---|---|
| JP | SHO 61-85920 | 5/1986 |
| JP | HEI 1-265937 | 10/1989 |
| JP | HEI 6-046999 | 2/1994 |
| JP | HEI 6-047003 | 2/1994 |
| JP | 07-194557 | 8/1995 |
| JP | HEI 10-71122 | 3/1998 |
| JP | HEI 10-108836 | 4/1998 |
| JP | HEI 10-155742 | 6/1998 |
| JP | 2005160548 A * | 6/2005 |

* cited by examiner

OPHTHALMIC APPARATUS

BACKGROUND OF THE INVENTION

1. Field of the Invention

The present invention relates to an ophthalmic apparatus for measuring and examining different eye characteristics of an eye of an examinee, more particularly to an ophthalmic apparatus for measuring and examining intraocular pressure and other eye characteristics.

2. Description of Related Art

In ophthalmologic diagnoses, different eye characteristics such as eye refractive power, a corneal shape and intraocular pressure are measured and examined in general (photographing of a fundus or the like is included therein). And, dedicated ophthalmic apparatuses are in widespread use, each of which objectively measures and examines the eye characteristics individually. However, the individual measurements and examinations by each dedicated apparatus bring trouble in relocation of an examiner and an examinee between the apparatuses and cause a waste of installation spaces. Therefore, proposed is a multifunction ophthalmic apparatus capable of measuring and examining the different eye characteristics.

For example, as an apparatus capable of measuring the intraocular pressure and the eye refractive power, conventionally proposed is an apparatus integrating an intraocular pressure measurement part storing an intraocular pressure measurement system with an eye refractive power measurement part storing an eye refractive power measurement system which are vertically arranged (see Japanese Patent Application Unexamined Publication No. Hei1-265937).

However, the conventional apparatus described above has a constitution where the measurement parts are integrally brought in vertical movements, and alignment in the vertical direction of the measurement parts with an eye of an examinee is performed respectively. Therefore, a larger amount of vertical movements is required than the vertical movements of the measurement part of the dedicated apparatus, and this apparatus has problems such as upsizing of a moving mechanism and long time required for the alignment.

SUMMARY OF THE INVENTION

An object of the invention is to overcome the problems described above and to provide, in a multifunction ophthalmic apparatus with a capability of measuring and examining different eye characteristics, an ophthalmic apparatus capable of performing respective measurements and examinations efficiently.

To achieve the objects and in accordance with the purpose of the present invention, an ophthalmic apparatus has an intraocular pressure measurement part including a blowing unit which blows a fluid to a cornea via a nozzle for measuring intraocular pressure of an eye of an examinee, a reflection member, having a reflection surface, which is arranged insertably and removably between the eye and the nozzle, an eye characteristic examination part in which an examination optical system, which photo-receives reflection light from the eye reflected by the reflection member for examining an eye characteristic, is arranged, a main body in which the measurement part and the examination part are arranged, a first moving unit which moves the main body with respect to the eye in a working distance direction, a second moving unit which moves the measurement part with respect to the main body in the working distance direction, a third moving unit which performs insertion and removal of the reflection member between the eye and the nozzle, a mode switching device for emitting a switching signal to switch between a first mode for examining the eye characteristic and a second mode for measuring the intraocular pressure, and a movement control unit which controls each driving of the second and the third moving units based on the switching signal.

In another aspect of the present invention, an ophthalmic apparatus has an intraocular pressure measurement part including an blowing unit which blows a fluid to a cornea via a nozzle for measuring intraocular pressure of an eye of an examinee, an eye characteristic examination part in which an examination optical system, which photo-receives reflection light from the eye for examining an eye characteristic, is arranged, a main body in which the measurement part and the examination part are arranged, a mobile base on which the main body is movably arranged, a first moving unit, having a movement operating member, which moves the mobile base with respect to the eye in a working distance direction through operation of the operating member, a second moving unit which moves the main body with respect to the mobile base in the working distance direction, a third moving unit which moves the measurement part with respect to the main body in the working distance direction, a detection unit which detects that the mobile base is located at a rear reference position in a direction away from the eye to emit a detection signal, a mode switching device for emitting a switching signal to switch between a first mode for examining the eye characteristic and a second mode for measuring the intraocular pressure, and a movement control unit which controls driving of the third moving unit so as to move the measurement part near to the eye, based on the detection signal of the detection unit and the switching signal from the first mode to the second mode.

Yet, in another aspect of the present invention, an ophthalmic apparatus further has an intraocular pressure measurement part including an blowing unit which blows a fluid to a cornea via a nozzle for measuring intraocular pressure of an eye of an examinee, an eye characteristic examination part in which an examination optical system, which photo-receives reflection light from the eye for examining an eye characteristic, is arranged, a main body in which the measurement part and the examination part are arranged, a first moving unit which moves the main body with respect to the eye in a working distance direction, a second moving unit which moves the measurement part with respect to the main body in the working distance direction, a mode switching device for emitting a switching signal to switch between a first mode for examining the eye characteristic and a second mode for measuring the intraocular pressure, and a movement control unit which controls driving of the second moving unit so as to move the measurement part near to the eye based on the switching signal from the first mode to the second mode, and controls the driving of the second moving unit so as to move the measurement part away from the eye based on the switching signal from the second mode to the first mode.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and together with the description, serve to explain the objects, advantages and principles of the invention. In the drawings.

DETAILED DESCRIPTION OF THE PREFERRED EMBODIMENTS

Figure 1:
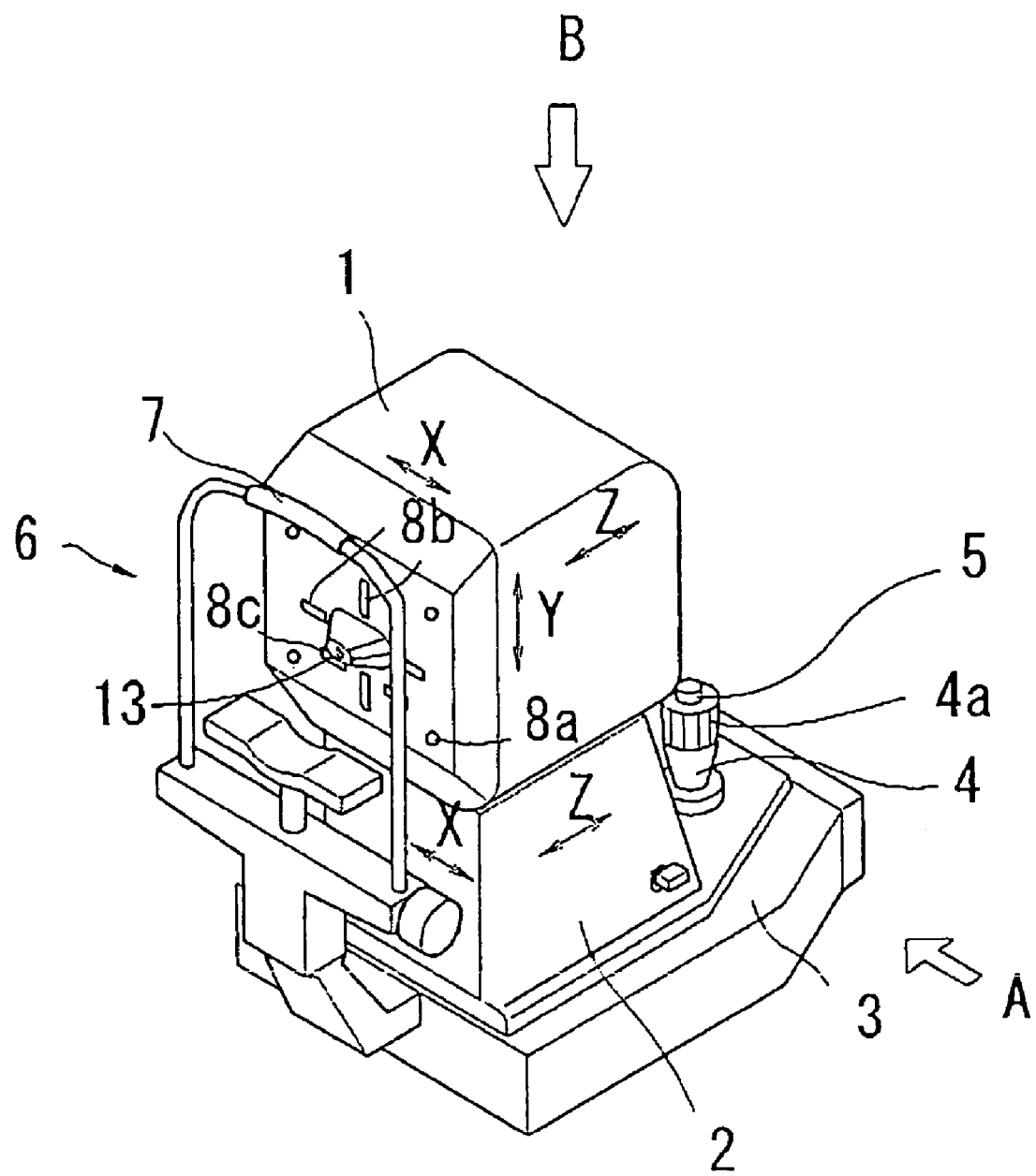
FIG. 1 is a view showing a schematic configuration of an ophthalmic apparatus consistent with the present invention.

A detailed description of one preferred embodiment of an ophthalmic apparatus embodied by the present invention is provided below with reference to the accompanying drawings. In this embodiment, a multifunction apparatus which measures intraocular pressure, eye refractive power and a corneal shape will be taken as an example. FIG. 1 is a view showing as schematic configuration of an ophthalmic measurement apparatus consistent with the present invention.

A mobile base 2, on which a main body 1 is provided, is arranged on a base 3 movably in a right/left direction (referred to as an X-direction hereinafter) and a back/forth direction (a working distance direction, referred to as a Z-direction hereinafter). This movement is mechanically (or may be electrically) performed through operation of a joystick 4. Additionally, the main body 1 is arranged on the mobile base 2 movably in the X-direction, Z-direction, and an up/down direction (referred to as a Y-direction hereinafter). The movement in each direction is electrically performed based on a detection result on an alignment state of the main body 1 with an eye of an examinee. Further, the movement in the Y-direction is electrically performed also through operation of a rotation knob 4a of the joystick 4.

On the base 3, a face-supporting unit 6 for supporting a face of the examinee is fixedly provided. Further, a forehead rest 7, against which a forehead of the examinee is slightly pressed to be fixed, is provided to the face-supporting unit 6. A measurement starting switch 5 is provided at the top of the joystick 4. Projection windows 8a allow the passage of light from light sources 20 for anterior-segment illumination described later. Projection windows 8b allow the passage of light from light sources 80 for corneal shape measurement described later. Projection windows 8c allow the passage of light from light sources 85 for alignment in the Z-direction described later.

Figure 2:
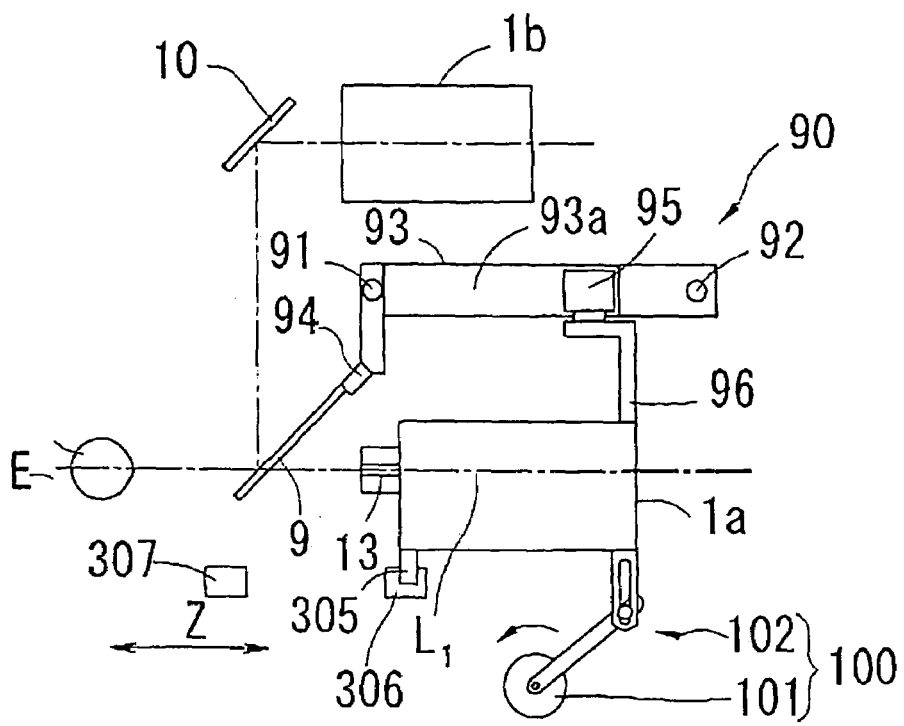
FIGS. 2A and 2B are views showing a schematic configuration of an inside of a main body when viewed from the side.
Figure 2:
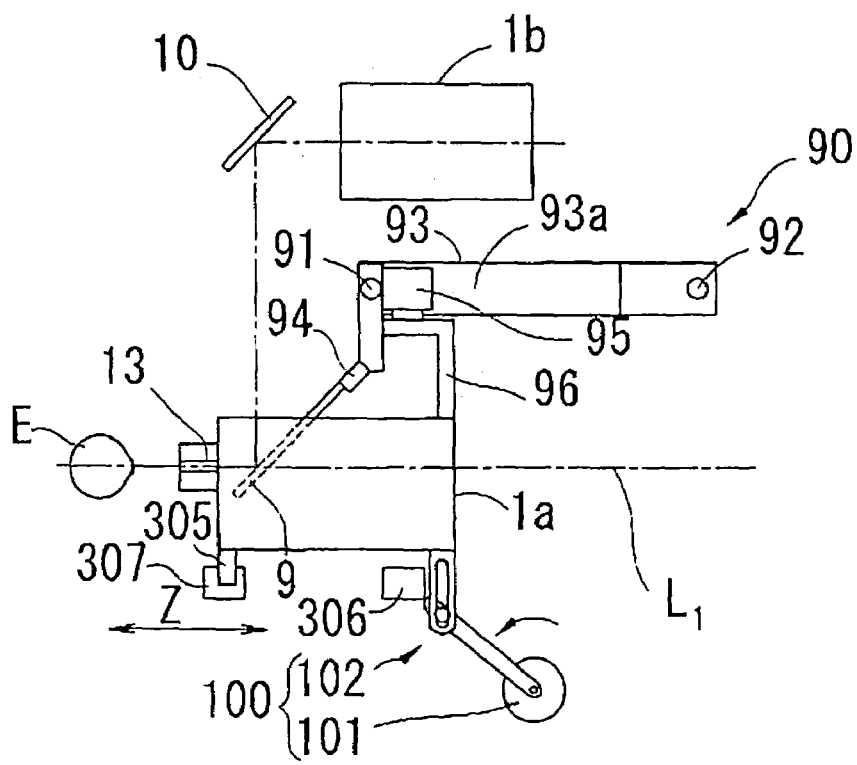
Figure 3A:
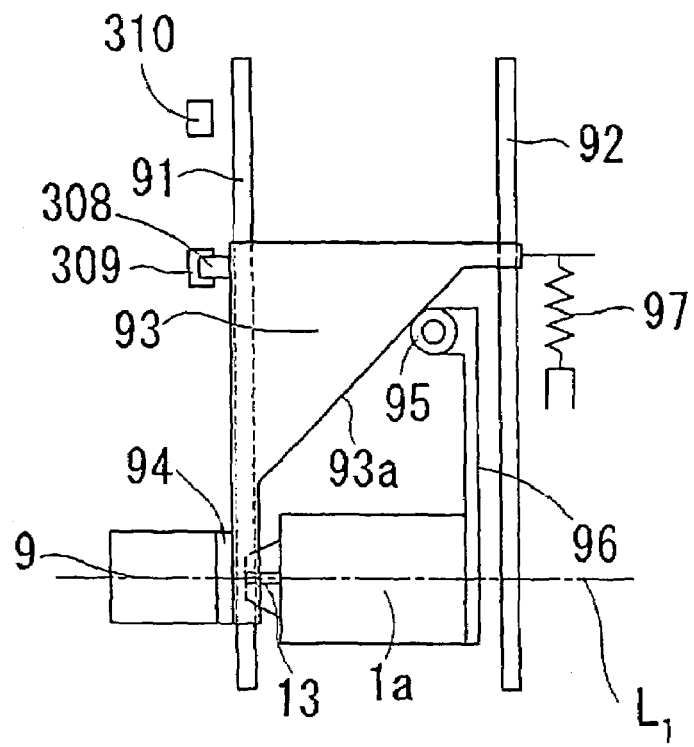
FIGS. 3A and 3B are views showing a schematic configuration of the inside of the main body when viewed from above.
Figure 3B:
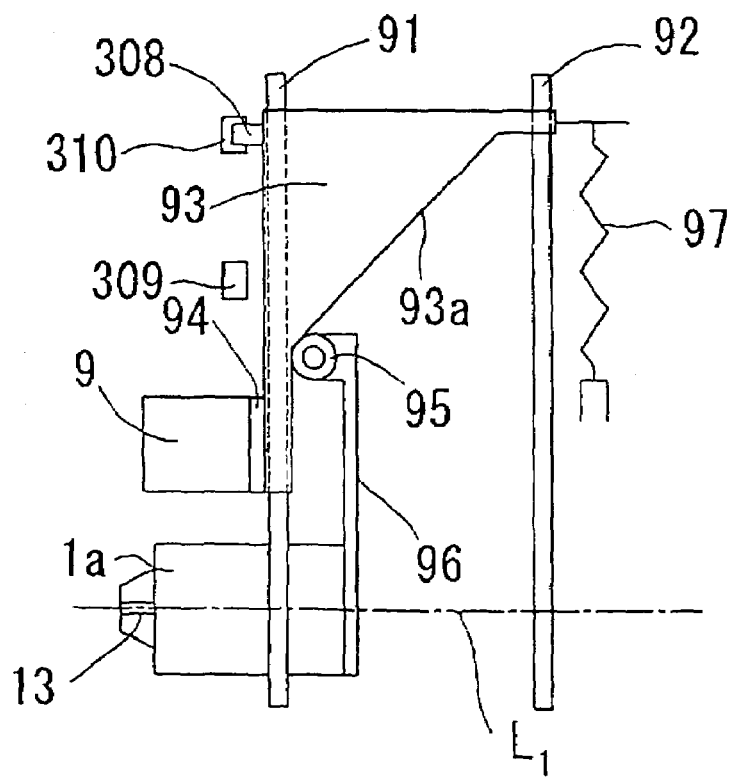

FIGS. 2A and 2b are views showing a schematic configuration of an inside of the main body 1 when viewed from the side (i.e., from a direction of the arrow A shown in FIG. 1) FIGS. 3A and 3B are views showing a schematic configuration of the inside of the main body 1 when viewed from above (i.e., from a direction of the arrow B shown in FIG. 1). Inside the main body 1, an intraocular pressure measurement part 1a for performing noncontact measurement of the intraocular pressure of an eye E of the examinee is arranged movably in the Z-direction, and an eye refractive power/corneal shape measurement part 1b for measuring the eye refractive power and the corneal shape of the eye E is fixedly arranged above the measurement part 1a. Further, a reflection mirror 9, a reflection mirror 10, a mirror moving unit 90, and a moving unit 100 for the measurement part 1a are arranged.

The moving unit 90 includes two guide rods 91 and 92 extending in the X-direction which are fixedly arranged inside the main body 1, a moving member 93 through which the guide rods 91 and 92 pass, a mirror holding member 94 which is fixedly mounted on the moving member 93 to hold the mirror 9, a roller 95 in contact with an oblique surface 93a which is formed on a side of the moving member 93, a connecting member 96 extending in the X-direction, at the tip of which the roller 95 is mounted and at the other tip of which the measurement part 1a is fixedly mounted, an energization member (bias member) 97 such as a spring for energizing (biasing) the moving member 93a toward the measurement part 1a. In addition, the moving unit 100 includes a motor 101 and a crank mechanism 102 which connects the motor 101 with the measurement part 1a.

The measurement part 1a is moved in parallel in the Z-direction via the crank mechanism 102 by driving of the motor 101. At this time, the connecting member 96 and the oblique surface 93a of the moving member 93 act as a guide for the movement. The oblique surface 93a, as shown in FIGS. 3A and 3B, extends in a direction intersecting obliquely with the Z-direction; therefore, when the measurement part 1a is moved from a retreat position in FIG. 2A to a measurement reference position in FIG. 2B, the moving member 93 is pushed by the roller 95 (the connecting member 96) to move along the guide rods 91 and 92 from a state in FIG. 3A to a state in FIG. 3B. Thereby, the mirror 9 fixedly mounted on the moving member 93 via the mirror holding member 94 is also moved from a state in FIG. 3A where the mirror 9 is inserted in front of a nozzle 13 of the measurement part 1a (i.e. between the eye E and the nozzle 13) to a state in FIG. 3B where the mirror 9 is removed therefrom.

In contrast, when the measurement part 1a is moved by the driving of the motor 101 from the measurement reference position in FIG. 2B to the retreat position in FIG. 2A, the moving member 93 is moved by energization power of the energization member 97 from the state in FIG. 3B to the state in FIG. 3A. Thereby, the mirror 9 is also moved from the state in FIG. 3B to the state in FIG. 3A.

Incidentally, a constitution may be employed where the mirror 9 is inserted and removed in front of the nozzle 13 by a moving mechanism for flipping up the mirror 9 in the upward direction. In this case, however, if positional deviation (angle deviation of a reflection surface of the mirror 9 from a measurement optical axis L1) is generated when the mirror 9 is re-inserted in front of the nozzle 13, optical axis deviation occurs to reflection light from the eye E, which is reflected by the mirror 9 and guided to a measurement part 1b, influencing measurement accuracy. On the other hand, if a constitution is employed where the mirror 9 is moved in a parallel direction to its reflection surface as with this embodiment, even if the positional deviation is generated to some degree when the mirror 9 is re-inserted in front of the nozzle 13, the influence to the measurement accuracy for the measurement part 1b may be suppressed, since the angle of the reflection surface of the mirror 9 with the optical axis L1 is maintained.

In addition, prisms instead of the mirrors 9 and 10, and a prism holding member instead of the mirror holding member 94 are used to enable the prisms to be moved in conjunction with the measurement part 1a through a similar mechanism to the moving unit 90.

Besides, in this embodiment, the measurement part 1a and the mirror 9 are synchronously moved by a driving force of the motor 101. However, they may be moved by separate driving forces.

Figure 4:
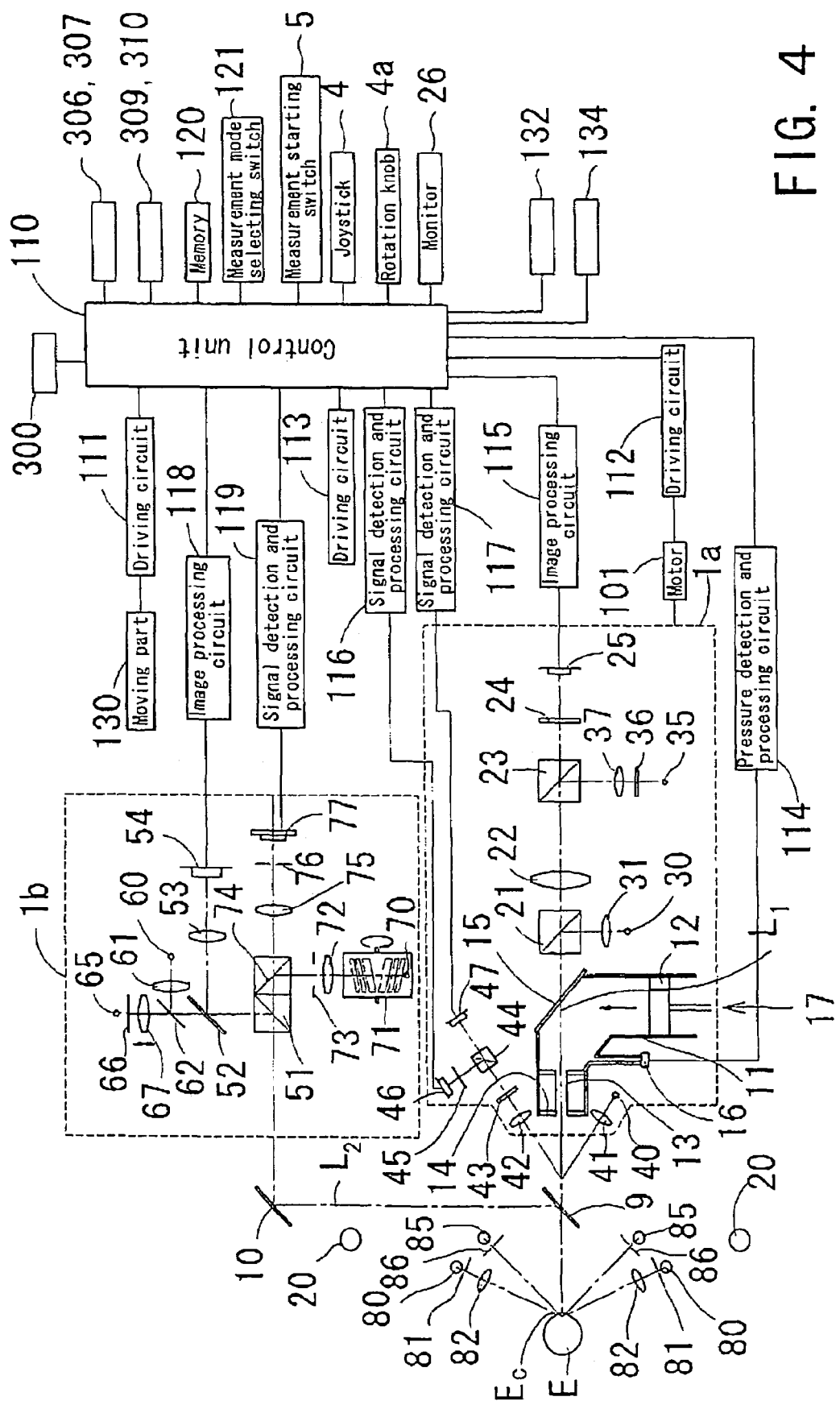
FIG. 4 is a view showing a schematic configuration of optical systems arranged inside the main body, a fluid blowing mechanism in an intraocular pressure measurement part, and a control system of the present apparatus.

FIG. 4, is a view showing a schematic configuration of optical systems arranged inside the main body 1, a fluid blowing mechanism in the measurement part 1a, and a control system of the present apparatus.

Firstly, an air (fluid) blowing mechanism 17 in the measurement part 1a will be described. Reference numeral 11 indicates a cylinder for air compression. A piston 12 is moved inside the cylinder 11 by driving force of an unillustrated rotary solenoid. The air compressed inside the cylinder 11 by the movement of the piston 12 is blown from the nozzle 13 to a cornea Ec of the eye E. A transparent glass plate 14 holds the nozzle 13. A transparent glass plate 15 is provided behind the nozzle 13. Behind the glass plate 15, optical systems for observation and alignment described later are arranged. A pressure sensor 16 detects pressure inside the cylinder 11.

Next, the optical systems in the measurement part 1a will be described. In this regard, when using the measurement part 1a (at the time of intraocular pressure measurement), the mirror 9 is moved by the aforementioned moving units 90 and 100 to the retreat position where it does not influence the intraocular pressure measurement (in the state in FIG. 3B).

Four infrared light sources 20 for anterior-segment illumination are arranged having the optical axis L1 coincident with an axial line of the nozzle 13 as their center. An image of an anterior-segment of the eye E formed by the light sources 20 is transmitted through the glass plate 15, a half mirror 21, an objective lens 22, a dichroic mirror 23, and a filter 24, each arranged on the optical axis L1, to be picked up by a CCD camera 25 being an image-pickup element. Besides, the dichroic mirror 23 has a property of transmitting infrared light and reflecting visible light. Additionally, the filter 24 has a property of transmitting light from the light sources 20 and a light source 30 described later, and not transmitting light from a light source 40 described later. The image of the anterior-segment of the eye E picked up by the camera 25 is displayed on a monitor 26.

The infrared light source 30 is for alignment in the X- and Y-direct ions, and the light therefrom is transmitted through a projection lens 31, the half mirror 21, and the glass plate 15, to be projected onto the cornea Ec from the front. An image of corneal reflection by the light source 30 is transmitted through the glass plate 15 to the filter 24 to be picked up by the camera 25, and is utilized in the alignment in the X- and Y-directions. Besides, an image of corneal reflection by the light sources 20 may be utilized in the alignment in the X- and Y-directions (for details, see U.S. Pat. No. 6,022,108 corresponding to Japanese Patent Application Unexamined Publication No. Hei10-71122). Reference numeral 35 indicates a visible light source for fixation target projection, and light from a fixation target 36 illuminated by the light source 35 is transmitted through a projection lens 37, the dichroic mirror 23, the objective lens 22, the half mirror 21, and the glass plate 15, to head for the eye E.

The infrared light source 40 is for detection of a deformation state of the cornea Ec, and the light therefrom is made an approximately parallel light bundle by a collimator lens 41 to be projected onto the cornea Ec. An image of corneal reflection by the light source 40 is transmitted through a photo-receiving lens 42, a filter 43, a half mirror 44, and a pinhole plate 45, to be photo-received on a photo-detector 46. The filter 43 has a property of transmitting the light from the light source 40 and not transmitting the light from the light sources 20 and 30. These optical systems are arranged such that a photo-receiving amount of the photo-detector 46 is at the maximum when the cornea Ec is in a predetermined deformation state (a flat state).

In addition, the light source 40 and the collimator lens 41 are also utilized in alignment in the Z-direction, and the image of corneal reflection by the light source 40 is transmitted through the photo-receiving lens 42 to the half mirror 44 and enters a one-dimensional position detector 47 such as a PSD or a line sensor. When the eye E (cornea Ec) is moved in the Z-direction, an entering position of the image of corneal reflection by the light source 40 is also moved on the position detector 47. Therefore, an alignment state in the Z-direction with respect to the eye E may be detected based on an output signal from the position detector 47.

Incidentally, for the sake of illustration, FIG. 4 shows such that the optical system for the detection of the deformation state of the cornea Ec and that for the detection of the alignment state in the Z-direction are vertically arranged; however, they are primarily arranged horizontally with respect to the eye of the examinee.

Next, the optical systems in the measurement part 1b will be described. When the measurement part 1b is used (at the time of eye refractive power/corneal shape measurement), the mirror 9 is moved by the aforementioned moving units 90 and 100 to the measurement reference position in front of the nozzle 13 (in the state in FIG. 3A).

The image of the anterior-segment of the eye E by the light sources 20 is reflected by the mirror 9, and is transmitted through the mirror 10, a half mirror 51, a half mirror 52, and an image forming lens 53, each arranged on a measurement optical axis L2 made coaxial with the optical axis L1 by the mirror 9, to be picked up by a CCD camera 54 being an image-pickup element. The image of the anterior-segment of the eye E picked up by the camera 54 is displayed on the monitor 26.

Reference numeral 60 indicates an infrared light source for the alignment in the X- and Y-directions, and light therefrom is transmitted through a projection lens 61, a dichroic mirror 62, the half mirror 52, the half mirror 51, the mirror 10 and the mirror 9, to be projected onto the cornea Ec from the front. Incidentally, the dichroic mirror 62 has a property of transmitting visible light and reflecting infrared light. An image of corneal reflection by the light source 60 is transmitted through the mirror 9 to the image forming lens 53 to be picked up by the camera 54, and is utilized in the alignment in the X- and Y-directions. Besides, the image of corneal reflection by the light sources 20 may also be utilized in the alignment in the X- and Y-directions. Reference numeral 65 indicates a visible light source for fixation target projection, and light from a fixation target 66 illuminated by the light source 65 is transmitted through a projection lens 67, the dichroic mirror 62, the half mirror 52, the half mirror 51, the mirror 10 and the mirror 9 to head for the eye E. In addition, the projection lens 67 is moved in the direction of an optical axis, so that the eye E is fogged.

Reference numeral 70 indicates an infrared light source for eye refractive power measurement, and light therefrom passes through slits provided in a rotation sector 71, and is transmitted through a projection lens 72, a diaphragm 73, a half mirror 74, the half mirror 51, the mirror 10, and the mirror 9, to be projected onto a fundus of the eye E while being scanned. Reflection light from the fundus is transmitted through the mirror 9, the mirror 10, the half mirror 51, the half mirror 74, a photo-receiving lens 75 and a diaphragm 76, and is photo-received on a photo-receiving part 77 provided with a plurality of pairs of photodetectors. Incidentally, in connection with the optical system for the eye refractive power measurement, see U.S. Pat. No. 5,907,388 corresponding to Japanese Patent Application Unexamined Publication No. Hei10-108836 for details.

Besides, an image of corneal reflection by the light source 70 may be utilized in the alignment in the X- and Y-directions. In this case, the light source 60, the projection lens 61, and the dichroic mirror 62 may be omitted.

Four infrared light sources 80 for the corneal shape measurement and the alignment in the Z-direction are arranged having the optical axis L1 as their center. Two of them are arranged in a horizontal direction of the apparatus, and the other two of them are arranged in a vertical direction of the apparatus, in order that each of their projection optical axes intersects at a predetermined angle with the optical axis L1. Light from the light sources 80 is transmitted through spot diaphragms 81, and collimating lenses 82, to be projected onto the cornea Ec. An image of corneal reflection by the light sources 80 is transmitted through the mirror 9, the mirror 10, the half mirror 51, the half mirror 52, and the image forming lens 53, to be picked up by the camera 54. Besides, for details of the optical system for the corneal shape measurement, see Japanese Patent No. Hei1-19896 (Japanese Patent Application Unexamined Publication No. Sho61-85920).

Two infrared light sources 85 for the alignment in the Z-direction are arranged having the optical axis L1 as their center. Further, the light sources 85 are arranged in the horizontal direction of the apparatus so that each of their projection optical axes intersects at a predetermined angle with the optical axis L1. Light from the light sources 85 is transmitted through spot diaphragms 86 to be projected onto the cornea Ec. An image of corneal reflection by the light sources 85 is transmitted through the mirror 9, the mirror 10, the half mirror 51, the half mirror 52, and the image forming lens 53, to be picked up by the camera 54.

Since the light from the light sources 80 is made a parallel light bundle by the collimating lenses 82, even if a working distance (distance in the Z-direction) of the main body 1 with respect to the eye E is changed, a position of the image of corneal reflection is seldom changed. In contrast, since the light from the light sources 85 is a divergent light bundle, if the working distance is changed, a position of the image of corneal reflection is changed. Thus, an alignment state in the Z-direction may be detected from the positions of these images of corneal reflection (for details, see U.S. Pat. No. 5,463,430 corresponding to Japanese Patent Application Unexamined Publication No. Hei6-46999).

A control part 110 is connected with a driving circuit 111 for a moving part 130 which moves the main body 1 in the three-dimensional X-, Y- and Z-directions, a driving circuit 112 for the motor 101, a driving circuit 113 for the unillustrated rotary solenoid which moves the piston 12, a pressure detection and processing circuit 114 for the pressure sensor 16, an image processing circuit 115 for the camera 25, a signal detection and processing circuit 116 for the photo-detector 46, a signal detection and processing circuit 117 for the position detector 47, an image processing circuit 118 for the camera 54, a signal detection and processing circuit 119 for the photo-receiving part 77. In addition, the control part 110 is connected with a memory 120 for storing measured data and the like, the switch 5, a measurement-mode selecting switch 121, and the like.

The moving part 130 may be constituted such that an X-table movable in the X-direction is provided on a Y-table movable in the Y-direction, and a Z-table movable in the Z-direction is provided on the X-table, and then the main body 1 is mounted on the Z-table. The respective tables are moved by driving and controlling motors for movement in the respective X-, Y- and Z-directions. As a known constitution may be adopted for this kind of three-dimensional movement mechanism, detailed illustrations are omitted herein.

In the ophthalmic measurement apparatus having the aforementioned constitution, its operations will be described. The present apparatus includes a first mode in which only an eye refractive power/corneal shape measurement mode is performed, a second mode in which only an intraocular pressure measurement mode is performed, and a third mode in which the eye refractive power/corneal shape measurement mode and the intraocular pressure measurement mode are successively performed. In the third mode, the eye refractive power/corneal shape measurement mode is firstly performed, and then is automatically switched to perform the intraocular pressure measurement mode. This is because, if the intraocular pressure is measured first, an influence of the blow of the compressed air and the like possibly remains. Hereinafter, the third mode will be described.

The third mode is selected by the switch 121 to perform the alignment in the respective X-, Y- and Z-directions of the main body 1 with the eye E. As the image of the anterior-segment of the eye E picked up by the camera 54 is displayed on the monitor 26, the examiner performs rough alignment through the operation of the joystick 4 and the rotation knob 4a while observing the monitor 26. When the images of corneal reflection by the light sources 60, 80 and 85 are in a condition for picking up by the camera 54, the control part 110 drives and controls the moving part 130 via the driving circuit 111 and performs fine alignment in the respective X-, Y- and Z-directions of the main body 1 with the eye E.

Once the alignment state in the X-, Y- and Z-directions respectively falls within a predetermined permissible range, the control part 110 automatically controls to emit a trigger signal (or the examiner depresses the switch 5 to input the trigger signal in accordance with a display of alignment completion displayed on the monitor 26), the eye refractive power is obtained based on phase difference of output signals from each of the photodetectors in the photo-receiving part 77. In addition, the control part 110 controls to obtain a position of the image of corneal reflection by the light sources 80 and calculate the corneal shape, based on an output signal from the camera 54.

In the third mode, when the eye refractive power/corneal shape measurement satisfies a predetermined condition for measurement termination such that the predetermined number of measurement results are obtained respectively, the control part 110 automatically controls to emit a switching signal to the intraocular pressure measurement mode, and the eye refractive power/corneal shape measurement mode is switched to the intraocular pressure measurement mode. Based on the switching signal to the intraocular pressure measurement model the control part 110 drives and controls the motor 101 via the driving circuit 112 to move the measurement part 1a forward (in a direction near to the eye E), and thrusts the tip of the nozzle 13 from the front of the main body 1. At this time, the mirror 9 is removed from the front of the nozzle 13 in conjunction with the movement of the measurement part 1a, so that each image of corneal reflection by the light sources 40 and 30 is brought in a detectable state. When the image of corneal reflection by the light source 40 is in a state of entering the position detector 47, the control part 110 drives and controls the moving part 130 (or the motor 101, or both of the moving part 130 and the motor 101) based on a detection result on the image, and performs fine alignment in the Z-direction. Further, the control part 110 controls to switch the image displayed on the monitor 26 from that picked up by the camera 54 to that picked up by the camera 25 based on the switching signal to the intraocular pressure measurement mode. Furthermore, the moving part 130 is driven and controlled based on a detection result on the image of corneal reflection by the light source 30, which is picked up by the camera 25, to perform fine alignment in the X- and Y-directions.

Incidentally, a working distance at the time of the intraocular pressure measurement (a distance in the Z-direction from a corneal vertex to the tip of the nozzle 13 facing the eye of the examinee) is set to be shorter than a working distance at the time of the eye refractive power/corneal shape measurement (a distance in the Z-direction from the corneal vertex to the tip portion to the main body 1 facing the eye of the examinee). For example, in this apparatus, a working distance WD1 at the time of the eye refractive power/corneal shape measurement is about 35 mm while a working distance WD2 at the time of the intraocular pressure measurement is about 11 mm. When the measurement part 1a is moved forward, the tip of the nozzle 13 possibly contacts with the eye E. Therefore, preferably, the moving part 130 is driven and controlled to move the main body 1 once to a rear (a direction away from the eye E) reference position (e.g., which is set at the most rear side), and then the tip of the nozzle 13 is thrust by a fixed amount from the front of the main body 1. The thrust amount is for example set to be a difference between WD1 and WD2 (when WD1=about 35 mm and WD2=about 11 mm, the thrust amount is about 24 mm). After then, the main body 1 is moved in the Z-direction based on the detection result on the alignment state in the Z-direction by the position detector 47.

Further, in a case where a movable range of the main body 1 in the Z-direction is short, for reliably avoiding contact with the eye E due to the forward movement of the measurement part 1a, a constitution is preferably employed where the examiner moves the mobile base 2 backward through the operation of the joystick 4 to move the main body 1 sufficiently backward, and then moves the measurement part 1a forward. In this case, when the switching signal to the intraocular pressure measurement mode is emitted, an instruction message for backward movement of the mobile base 2 is displayed on the monitor 26. Then, after the mobile base 2 is detected to have moved to a rear reference position (e.g., which is set at the most rear side) (separately, a micro switch and the like for detecting that the mobile base 2 has been moved to the rear reference position is provided to the base 3), the control part 110 controls to move the measurement part 1a forward through the operation of the joystick 4 by the examiner. Once the alignment in the X-, Y- and Z-directions respectively of the measurement part 1a with the eye E falls within the permissible range, the control part 110 automatically controls to emit the trigger signal (or the examiner depresses the switch 5 to input the trigger signal in accordance with the display of alignment completion displayed on the monitor 26), and to drive the unillustrated rotary solenoid via the driving circuit 113. When the piston 12 is moved by driving the rotary solenoid, the air inside the cylinder 11 is compressed and blown from the nozzle 13 to the cornea Ec. The cornea Ec is gradually deformed y the blow of the compressed air, and when it reaches the flat state, the maximum amount of light enters the photo-detector 46. The control part 110 controls to calculate the intraocular pressure based on an output signal from the pressure sensor 16 and an output signal from the photo-detector 46.

In the aforementioned embodiment, the detection system of the alignment state in the Z-direction is provided for the measurement part 1b and the measurement part 1a respectively; however, if it is shared by both of the measurement parts, the components may be simplified. In this case, target projection systems employing the light sources 80 and 85 may be shared and the target detection systems may be comprised of the cameras 54 and 25, respectively; however, as the intraocular pressure measurement requires higher detection accuracy of the working distance than the refractive power measurement, a working distance detection system in the measurement part 1a (the target projection system including the light source 40 and the collimator lens 41, and the target detection system including the photo-receiving lens 42, the filter 43 and the position detector 47) may preferably be shared. This working distance detection system is separated from the measurement part 1a and is arranged in a housing of the main body 1 instead of the light sources 85. In addition, the half mirror 44 for corneal deformation detection, the pinhole plate 45, and the photo-detector 46 may also be arranged in combination with the working distance detection system.

In the sharing of the working distance detection system, since the working distance is different at the time of the eye refractive power/corneal shape measurement and at the time of the intraocular pressure measurement respectively as mentioned above, the control part 110 controls to switch also the working distances for the judgment of appropriateness of the alignment state, in accordance with the switching signal between the eye refractive power/corneal shape measurement mode and the intraocular pressure measurement mode. If the working distance WD1=about 35 mm in the eye refractive power/corneal shape measurement mode, and the working distance WD2=about 11 mm and the thrust amount of the tip of the nozzle 13=about 2.4 mm in the intraocular pressure measurement mode, the detection results obtained by the position detector 47, when judging whether proper working distances are attained, may be set to be the same in both of the measurement modes. In contrast, if the thrust amount of the tip of the nozzle 13 is not about 24 mm, in consideration of a difference in the thrust amount, the detection results obtained by the position detector 47, when judging whether proper working distances are attained, are set to be different to each other in both of the measurement modes.

In addition, since higher alignment accuracy is required in the intraocular pressure measurement than the eye refractive power/corneal shape measurement, the permissible range of the alignment state in the Z-direction (as well in the X- and Y-directions) in the intraocular pressure measurement mode is set to be narrower than that in the eye refractive power/corneal shape measurement mode. For example, the permissible range in the Z-direction is ±0.5 mm with respect to the proper working distance in the eye refractive power/corneal shape measurement mode while it is ±0.15 mm in the intraocular pressure measurement mode. For this reason, the control part 110 controls to switch also the permissible range for judging the alignment completion in accordance with the switching signal of the measurement mode.

Figure 5:
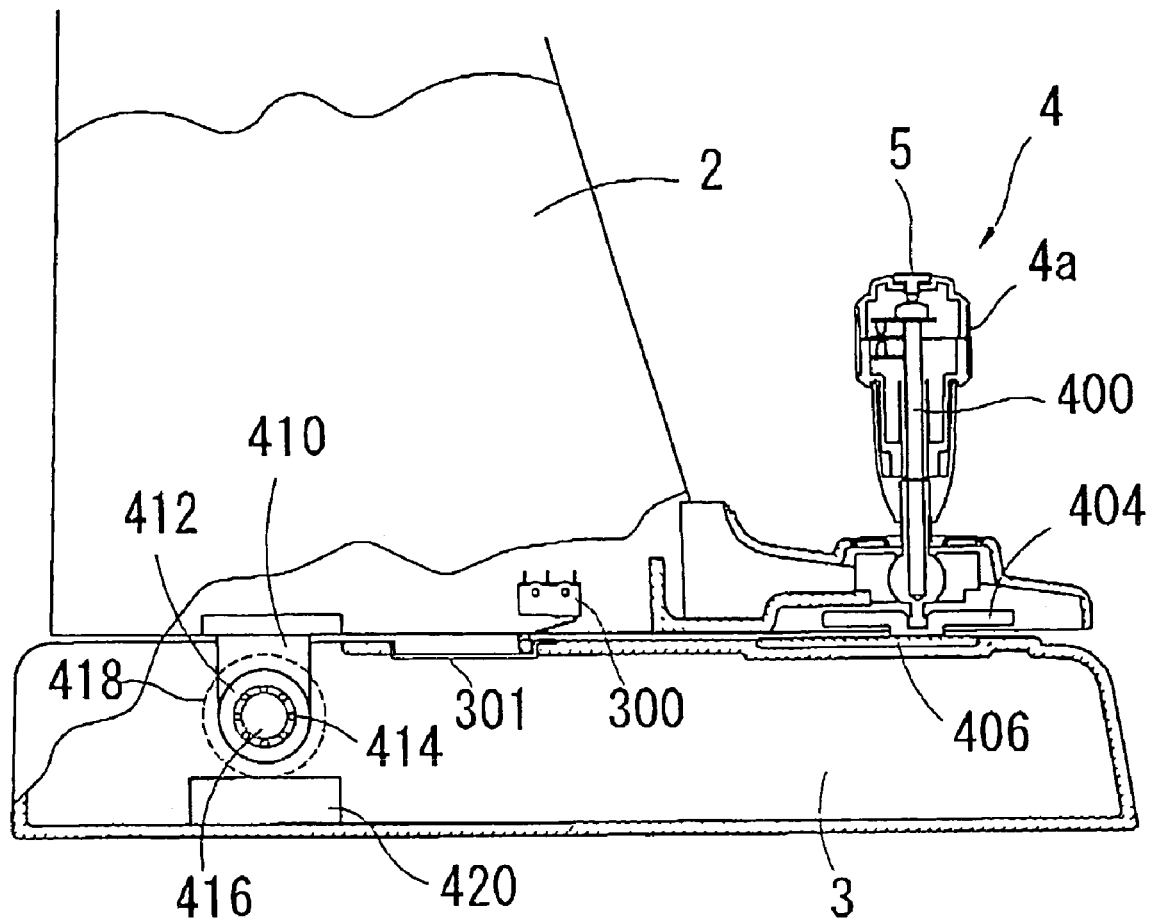
FIG. 5 is a view showing a schematic configuration of a moving mechanism of a mobile base and a detection mechanism of movement of the mobile base to a rear reference position.
Figure 6:
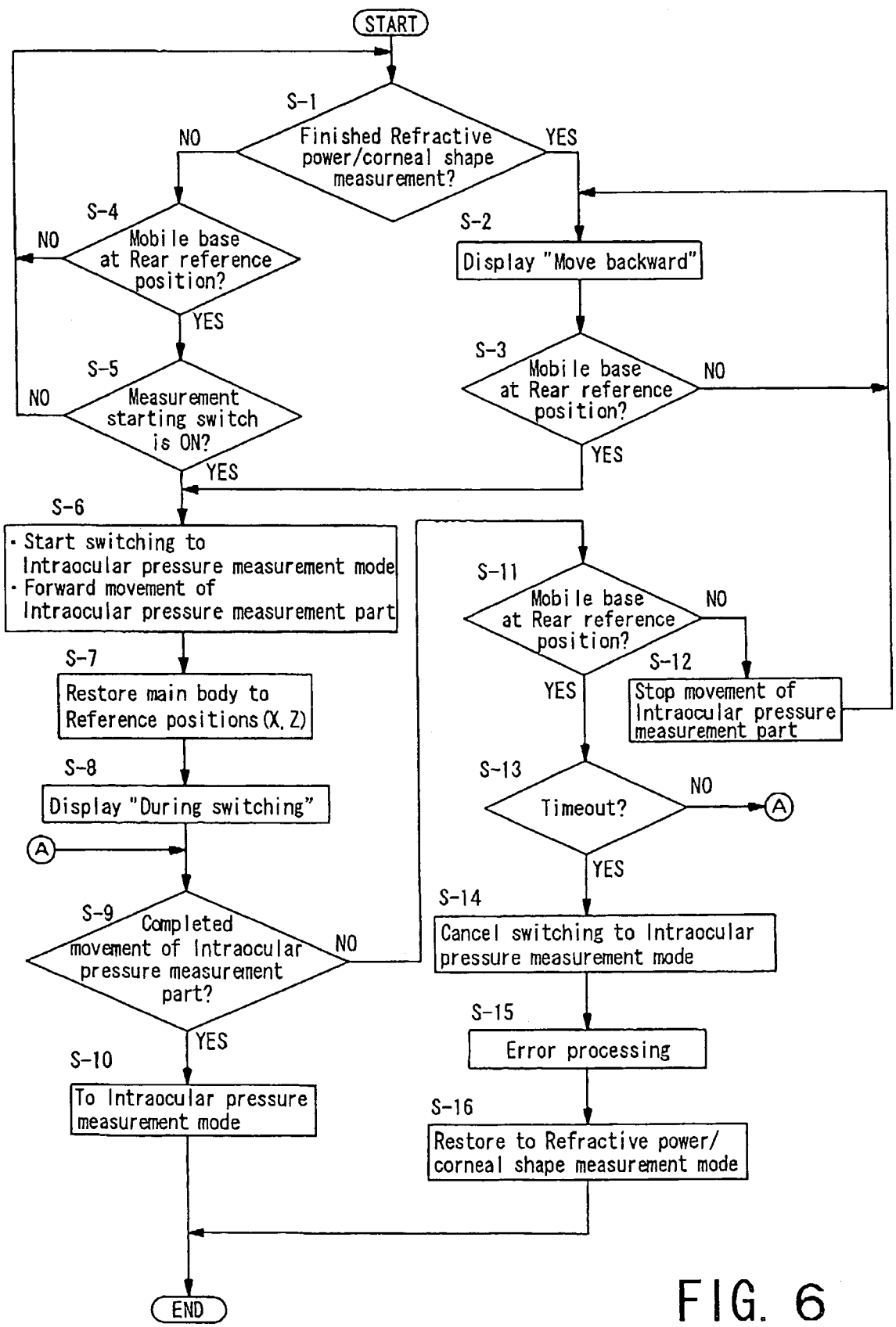
FIG. 6 is a flow chart illustrating operations in the case of a constitution where the intraocular pressure measurement part is moved forward after detecting that the mobile base is moved to the rear reference position.

FIG. 5 is a view showing a schematic configuration of a moving mechanism of the mobile base 2 and a mechanism for detecting that the mobile base 2 is moved to the rear reference position. FIG. 6 is a flowchart illustrating the operations in the case of a constitution where the measurement part 1a is moved forward after the detection of the movement of the mobile base 2 to the rear reference position through the operation of the joystick 4.

At the lower tip of a central shaft 400 in the joystick 4, a sliding plate 404 is provided. On the upper surface of the base 3, a friction plate 406 in contact with the sliding plate 404 is fixed, and the sliding plate 404 is movable on the friction plate 406. Further, a moving base 410 fixed to the mobile base 2 extends into the inside of the base 3 to reach a position at which a guide tube 412 is fixed. The guide tube 412 holds a shaft 416 slidably in its axial direction (the X-direction) via a ball bearing 414. Wheels 418 are rotatably provided at both ends of the shaft 416 and are enabled to roll in the Z-direction on a guide plate 420 provided on the inside bottom of the base 3. Owing to this constitution, when the examiner operates the joystick 4, the mobile base 2 is moved in the X- and Z-directions.

In addition, in this embodiment, the micro switch 300 detecting that the mobile base 2 is moved to the rear reference position is provided to the mobile base 2. Reference numeral 301 indicates a guide plate fixed to the base 3. When the mobile base 2 is moved to the rear reference position through the operation of the joystick 4, contacts of the micro switch 300 are arranged to be thrust by the guide plate 301 for detection.

As mentioned above, in the third measurement mode, once the measurement results on both of the eyes are obtained through the eye refractive power/corneal shape measurement to satisfy the predetermined condition for measurement termination, the instruction message for backward movement of the mobile base 2 is displayed on the monitor 26 (the steps S-1 and S-2). In accordance with the display, the examiner operates the joystick 4 to move the mobile base 2 backward, and when the mobile base 2 is moved to the rear reference position, the detection signal from the micro switch 300 (the step S-3) permits the switching from the eye refractive power/corneal shape measurement mode to the intraocular pressure measurement mode, and the measurement part 1a is moved forward (the steps S-6 to S-9).

Incidentally, the detection signal from the micro switch 300 is also utilized when switching to the intraocular pressure measurement mode during the process of the eye refractive power/corneal shape measurement mode in the third mode or when the first mode is switched to the second mode. If the switching to the intraocular pressure measurement mode is to be performed in these conditions, the mobile base 2 is moved to the rear reference position through the operation of the joystick 4 by the examiner. By the detection signal from the micro switch 300 (the step S-4), a permission message for switching of the measurement mode is displayed on the monitor 26 as well as a permission signal for switching to the intraocular pressure measurement mode is inputted. Then, in this case, when the examiner depresses the switch 5 provided to the joystick 4 (the step S-5), this is regarded as the switching signal of the measurement mode, and the measurement part 1a is moved toward the eye E (the steps S-6 to S-9). Detected that the mobile base 2 is moved to the rear reference position by the micro switch 300, the input signal from the switch 5 is utilized not as the trigger signal for measurement starting but as the switching signal to the intraocular pressure measurement mode (switching once to the intraocular pressure measurement in the third mode is included). Though the switching signal to the intraocular pressure measurement mode may be inputted also by the switch 121 provided to an operation panel or the like, the switch 5 provided to the joystick 4 may conveniently double as the switch 121. In other words, since the examiner operates the joystick 4 by hand when the mobile base 2 is moved, the measurement mode may be quickly and easily switched by depressing the switch 5 while holding the joystick 4. Further, since the joystick 4 may be maintained in a fixedly held state, the possibility may be reduced where the mobile base 2 happens to move upon switching of the measurement mode.

Further, during the forward movement of the measurement part 1a, when the mobile base 2 happens to move forward from the rear reference position because of a mistake by the examiner in the operation of the joystick 4 or other reasons, and the detection signal by the micro switch 300 is not received (in the case of NO in the step S-11), the control part 110 controls to stop the driving of the motor 101 for stopping the movement of the measurement part 1a to the measurement reference position (the step S-12). More securely, the measurement part 1a is returned backward. This may avoid contact with the nozzle 13 and reduce a sensation of fear to the examiner.

Furthermore, during the movement of the measurement part 1a in the Z-direction (especially forward), if a constitution is employed where a message informing this movement is displayed on the monitor 26 and an informing sound is generated at the same time, the examiner and the examinee may recognize that the nozzle 13 is in motion. The informing sound is generated by a sound generator 132. In this case, as the distance between the eye E and the nozzle 13 is decreased, intervals of the sounds generated intermittently are shortened or the informing sound is made loud, so that the movement of the nozzle 13 may be informed quantitatively and the sensation of fear to the examinee may be reduced. At the completion of the movement of the measurement part 1a, the informing sound is stopped and a message of movement completion is displayed on the monitor 26.

Further, when the working distance between the eye E and the nozzle 13 is detected, on the basis of the output signal from the position detector 47 or a signal from another distance sensor, to be less than or equal to a possible contact distance (e.g. less than or equal to 10 mm), the forward movement of the measurement part 1a is stopped. Furthermore, the measurement part 1a may be moved backward so that the working distance therebetween is more than or equal to the possible contact distance. At the same time, the display 26 displays as such, or the sound informs as such. This constitution enables avoiding contact with the nozzle 13.

Besides, in the aforementioned description, the main body 1 is moved (restored) to the rear reference position by the moving part 130 at the time of the switching to the intraocular pressure measurement mode. Also in the X-direction, the main body 1 is preferably moved (restored) to the reference position. This movement is performed by the switching signal of the measurement mode when the eye refractive power/corneal shape measurement mode is switched to the intraocular pressure measurement mode, or when a reverse switching thereof is performed. This enables reducing the possibility that the main body 1 reaches the movement limit during the automatic alignment and performing the automatic alignment after the switching of the measurement mode smoothly. Besides, in FIG. 4, reference numeral 134 indicates a detection system for detecting the movement limit and the reference position in the X-, Y- and Z-directions respectively, and this detection system may be constituted of photosensors, micro switches or the like which detect each travel position of the X-table, Y-table and Z-table in the moving part 130. The reference position of the main body 1 in the X-direction is in the middle of the movable range. Though the reference position in the Z-direction is set at the most rear end in the above description, it may also be in the middle of the movable range. As for the Y-direction, as an eye level once adjusted is deviated, the main body 1 may not necessarily be moved (restored) to the reference position.

Additionally, in the switching between the eye refractive power/corneal shape measurement mode and the intraocular pressure measurement mode, it is preferable that a mechanism which detects that the measurement part 1a is located at the retreat position and the measurement reference position as well as a mechanism which detects the insertion and removal of the mirror 9 with respect to an optical path are provided. That is to say, the measurement part 1a is provided with a light-shielding plate 305, so that a photosensor 306 detects that the measurement part 1a is moved to the retreat position in FIG. 3A and a photosensor 307 detects that the measurement part 1a is moved to the measurement reference position in FIG. 3B. Thereby, the measurement part 1a is checked if correctly moved to the retreat position and the measurement reference position. Further, the moving unit 90 is provided with a light-shielding plate 308, so that photosensors 309 and 310 check whether the mirror 9 is properly located at the measurement reference position on the optical axis L1 or is properly located at the retreat position outside the optical axis L1.

In the case of the switching from the eye refractive power/corneal shape measurement mode to the intraocular pressure measurement mode, if the photosensor 310 detects that the mirror 9 is retreated and the measurement part 1a is detected to have properly moved to the measurement reference position (the step S-9), the intraocular pressure measurement is allowed (the step S-10).

On the other hand, though the switching signal of the measurement mode is inputted and a fixed time required for the switching has elapsed, if not detected from the outputs by the photosensors 306, 307, 309 and 310 that the mirror 9 and the measurement part 1a are located at proper positions (in the case of YES at the step S-13), the movement of the measurement part 1a is stopped and the sound generator 132 generates the alarm sound at the same time, and an error message is displayed on the monitor 26 (the steps S-14 and S-15). Then, in this case, the mirror 9 and the measurement part 1a are restored to the positions in the previous measurement mode (a restore signal is outputted automatically). For example, in the switching from the eye refractive power/corneal shape measurement mode to the intraocular pressure measurement mode, when both of the mirror 9 and the measurement part 1a are not located at the proper positions, the measurement part 1a is restored to the retreat position and the mirror 9 is inserted into the optical axis L1, and then the eye refractive power/corneal shape measurement mode is restored (the step S-16). When the intraocular pressure measurement mode is switched to the eye refractive power/corneal shape measurement mode, the reverse operation thereof is performed. Thereby, even if one of the switching between the eye refractive power/corneal shape measurement and the intraocular pressure measurement results in error, at least one of the measurement is allowed avoiding a state where all the capabilities are unavailable.

The flowchart in FIG. 6 illustrates a case where the eye refractive power/corneal shape measurement is switched to the intraocular pressure measurement. On the other hand, in a case where the intraocular pressure measurement is switched to the eye refractive power/corneal shape measurement during the third measurement mode and other situations, and also in a case where the second mode is switched to the first mode, the detection signal of the micro switch 300 is utilized. In other words, as with the steps S-4 and S-5 previously mentioned, if the mobile base 2 is moved to the rear reference position through the operation of the joystick 4 by the examiner, the permission message of switching of the measurement mode is displayed on the monitor 26 and the permission signal for switching to the eye refractive power/corneal shape measurement mode is inputted. Once the switch 5 is depressed in this state, the switching signal therefrom is inputted as the switching signal of the measurement mode, and the measurement part 1a is restored to the retreat position. If the photosensors 306 and 309 detect that the measurement part 1a has properly moved to the retreat position and that the mirror 9 is properly located at the measurement reference position on the optical axis L1, the eye refractive power/corneal shape measurement is in an available state. As the switching may surely be performed by the switch 121 provided to the operation panel and the like, the switch 5 provided to the joystick 4 is used to enable quick and easy switching.

Besides, in a case where the switch 121 is used to perform switching from the intraocular pressure measurement to the eye refractive power/corneal shape measurement, the measurement part 1a is restored to the retreat position; therefore, it does not generally contact with the examinee. Thus, in this case, if the detection signal from the micro switch 300 is not received, the switching to the eye refractive power/corneal shape measurement mode is possible.

Incidentally, when the measurement mode is switched as mentioned above, the switching between observation images of the eye E picked up by the cameras 25 and 54 to be displayed on the monitor 26 is performed as follows. In the switching from the eye refractive power/corneal shape measurement mode to the intraocular pressure measurement mode, in the stage that the motor 101 is driven by the mode switching signal, the displayed image on the monitor 26 is switched from the image picked up by the camera 54 to the image picked up by the camera 25. In other words, due to the driving of the motor 101, the displayed image on the monitor 26 is switched in the stage that the mirror 9 is removed from the front of the nozzle 13 and the measurement part 1a starts to move toward the eye E. Thereby, even when the nozzle 13 starts thrusting, the examiner may confirm conditions of the eye E on the monitor 26.

On the other hand, in the switching from the intraocular pressure measurement mode to the eye refractive power/corneal shape measurement mode, the motor 101 is driven by the mode switching signal, and in the stage that the measurement part 1a is moved to the backward of the mirror 9 (in the stage that the mirror 9 is inserted into the front of the nozzle 13), the displayed image on the monitor 26 is switched from the image picked up by the camera 25 to the image picked up by the camera 54. This is because, in a case where the intraocular pressure measurement mode is switched to the eye refractive power/corneal shape measurement mode, if the image picked up by the camera 54 is switched in the stage that the mode switching signal is inputted, i.e. if the switching to the image picked up by the camera 54 in the measurement part 1b is performed before the nozzle 13 is moved to the backward of the mirror 9, the inside of the housing of the main body 1 is displayed on the monitor 26, and the conditions of the eye E cannot be confirmed on the monitor 26 by the examiner. For the timing of switching of the display on the monitor 26, a control signal for drive starting/drive stopping of the motor 101 which moves the measurement part 1a may be utilized, moreover, in this embodiment, the output signals from the photosensors 309 and 310 which detect the insertion and removal of the mirror 9 may be utilized. Owing to the switching control of the displayed image, the conditions of the eye E may be confirmed even during the movement of the measurement part 1a and the contact of the apparatus (the nozzle 13) with the face of the examinee may be avoided.

The above description has been made taking the multifunction apparatus of the intraocular pressure measurement and the measurement of the eye refractive power and the corneal shape as an example; however, it may be applied to a multifunction apparatus of the measurement of any one of the refractive power and the corneal shape, and the measurement and examination of other eye characteristics (including fundus photographing, sectional photographing of the anterior-segment of the eye, and the like).

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
   an intraocular pressure measurement part including a blowing unit which blows a fluid to a cornea via a nozzle for measuring intraocular pressure of an eye of an examinee;
   a reflection member, having a reflection surface, which is arranged insertably and removably between the eye and the nozzle;
   an eye characteristic examination part in which an examination optical system, which photo-receives reflection light from the eye reflected by the reflection member for examining an eye characteristic, is arranged;
   a main body in which the measurement part and the examination part are arranged;
   a first moving unit which moves the main body with respect to the eye in a working distance direction;
   a second moving unit which moves the measurement part with respect to the main body in the working distance direction;
   a third moving unit which performs insertion and removal of the reflection member between the eye and the nozzle;
   mode switching means for emitting a switching signal to switch between a first mode for examining the eye characteristic and a second mode for measuring the intraocular pressure; and
   a movement control unit which controls each driving of the second and the third moving units based on the switching signal.

2. The ophthalmic apparatus according to claim 1, wherein the movement control unit controls driving of the first moving unit so as to move the main body away from the eye, controls the driving of the second moving unit so as to move the measurement part near to the eye, and controls the driving of the third moving unit so as to remove the reflection member from between the eye and the nozzle, based on the switching signal from the first mode to the second mode.

3. The ophthalmic apparatus according to claim 1, wherein the movement control unit controls the driving of the second moving unit so as to move the measurement part near to the eye and controls the driving of the third moving unit so as to remove the reflection member from between the eye and the nozzle, based on the switching signal from the first mode to the second mode, and controls the driving of the second moving unit so as to move the measurement part away from the eye and controls the driving of the third moving unit so as to insert the reflection member between the eye and the nozzle, based on the switching signal from the second mode to the first mode.

4. The ophthalmic apparatus according to claim 3, further comprising:
   a first image-pickup unit, arranged in the examination part, which picks up an image of the eye via the reflection member;
   a second image-pickup unit, arranged in the measurement part, which picks up an image of the eye via the nozzle;
   a display unit which displays a first image being the image picked up by the first image-pickup unit and a second image being the image picked up by the second image-pickup unit; and
   a display control unit which controls the display unit so as to switch a display between the first image and the second image, based on movement of at least one of the measurement part and the reflection member.

5. The ophthalmic apparatus according to claim 3, further comprising a detection unit which detects at least one of whether the measurement part is located at a measurement reference position and whether the reflection member is located at an examination reference position,
   wherein the movement control unit controls each driving of the second and the third moving units based on a detection result obtained by the detection unit.

6. The ophthalmic apparatus according to claim 1, wherein the third moving unit moves the reflection member in a parallel direction to its reflection surface.

7. An ophthalmic apparatus comprising:
   an intraocular pressure measurement part including a blowing unit which blows a fluid to a cornea via a nozzle for measuring intraocular pressure of an eye of an examinee;
   an eye characteristic examination Part in which an examination optical system, which photo-receives reflection light from the eye for examining an eye characteristic, is arranged;
   a main body in which the measurement part and the examination part are arranged;
   a mobile base on which the main body is movably arranged;
   a first moving unit, having a movement operating member, which moves the mobile base with respect to the eye in a working distance direction through operation of the operating member;
   a second moving unit which moves the main body with respect to the mobile base in the working distance direction;
   a third moving unit which moves the measurement part with respect to the main body in the working distance direction;
   mode switching means for emitting a switching signal to switch between a first mode for examining the eye characteristic and a second mode for measuring the intraocular pressure;
   a detection unit which detects that the mobile base is located at a rear reference position set in a direction away from the eye with respect to a position of the mobile base at the time of examining in the first mode to emit a detection signal;
   a movement control unit which controls driving of the third moving unit so as to move at least a nozzle of the measurement part near to the eye by a predetermined distance with respect to the main body, based on the detection signal of the detection unit obtained after emission of the switching signal from the first mode to the second mode;
   a reflection member, arranged insertably and removably between the eye and the nozzle, for guiding the reflection light from the eye to the examination optical system; and a fourth moving unit which performs insertion and removal of the reflection member between the eye and the nozzle, wherein the movement control unit controls driving of the fourth moving unit so as to remove the reflection member between the eye and the nozzle, based on the detection signal of the detection unit obtained after emission of the switching signal from the second mode to the first mode.

* * * * *